(12) United States Patent
Tang

(10) Patent No.: US 12,213,980 B2
(45) Date of Patent: Feb. 4, 2025

(54) APPLICATION OF PDE9A INHIBITOR IN PREPARATION OF PRODUCTS HAVING ELEVATED TREG CONTENT, DRUGS FOR PREVENTING AND TREATING INFLAMMATORY BOWEL DISEASE AND HEALTH CARE PRODUCTS

(71) Applicant: ZHEJIANG UNIVERSITY, Zhejiang (CN)

(72) Inventor: Huifang Tang, Zhejiang (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 1033 days.

(21) Appl. No.: 17/258,910

(22) PCT Filed: Jul. 9, 2019

(86) PCT No.: PCT/CN2019/095291
§ 371 (c)(1),
(2) Date: Jan. 8, 2021

(87) PCT Pub. No.: WO2020/011168
PCT Pub. Date: Jan. 16, 2020

(65) Prior Publication Data
US 2021/0322423 A1 Oct. 21, 2021

(30) Foreign Application Priority Data
Jul. 10, 2018 (CN) .......................... 201810751621.1

(51) Int. Cl.
A61K 31/51 (2006.01)
A61K 31/519 (2006.01)
A61P 1/16 (2006.01)

(52) U.S. Cl.
CPC .............. *A61K 31/519* (2013.01); *A61P 1/16* (2018.01)

(58) Field of Classification Search
CPC .................................................. A61K 31/519
See application file for complete search history.

(56) References Cited

U.S. PATENT DOCUMENTS
2002/0007046 A1   1/2002   Fisher et al.

FOREIGN PATENT DOCUMENTS
CN   103052639 A   4/2013
CN   105669680 A   6/2016
WO   WO-2016/149218 A1   9/2016

OTHER PUBLICATIONS

How To Prevent Crohn's Disease by Erica Meier [online] retrieved from the internet, published on Feb. 15, 2023, URL: https://www.health.com/crohns-disease-prevention-7097735.*
Verhoest et al., "Design and Discovery of 6-[(3S, 4S)-4-Methyl-1-(pyrimidin-2-ylmethyl)pyrrolidin-3-yl]-1-(tetrahydro-2H-pyran-4-yl)-1, 5-dihydro-4H-pyrazolo[3, 4-d]pyrimidin-4-one (PF-04447943), a Selective Brain Penetrant PDE9A inhibitor for the Treatment of Cognitive Disease," *Journal of Medicinal Chemistry*, vol. 55, pp. 9045-9054, 2012.
Wang et al., "Identification and characterization of a new human type 9 cGMP-specific phosphodiesterase splice variant (PDE9A5). Differential tissue distribution and subcellular localization of PDE9A variants," *Gene*, vol. 314, pp. 15-27, 2003.
Hutson et al., "The selective phosphodiesterase 9 (PDE9) inhibitor PF-04447943 (6-[(3S,4S)-4-methyl-1-(pyrimidin-2-ylmethyl)pyrrolidin-3-yl]-1-(tetrahydro-2H-pyran-4-yl)-1,5-dihydro-4H-pyrazolo[3,4-d]pyrimidin-4-one) enhances synaptic plasticity and cognitive function in rodents," *Neuropharmacology*, vol. 61, pp. 665-676, 2011.
Barbosa, M. C., et al., "The Effect of a Selective Inhibitor of Phosphodiesterase-9 on Oxidative Stress, Inflammation and Cytotoxicity in Neutrophils from Patients with Sickle Cell Anaemia," Basic & clinical pharmacology & toxicology, 118(4), 2016, 271-278 <https://doi.org/10.1111/bcpt.12487>.
Wei, Xiaowei et al., "Progresses on the role of TNF receptors in the pathogenesis of IBD," Journal of Medical Postgraduates, vol. 22. No. 4, pp. 443-446, Apr. 30, 2009 (Apr. 30, 2009).
International Search Report mailed Oct. 30, 2019 for PCT/CN2019/095291.
Written Opinion mailed Oct. 30, 2019 for PCT/CN2019/095291 [non-English language].

* cited by examiner

*Primary Examiner* — Shawquia Jackson
(74) *Attorney, Agent, or Firm* — Banner & Witcoff, Ltd.

(57) ABSTRACT

The present invention relates to the field of medicine, and related to an application of a PDE9A inhibitor in the preparation of products having an elevated Treg content, drugs for preventing and treating inflammatory bowel disease, and health care products. The PDE9A inhibitor may improve the secretion of mucosal mucus in an intestinal tract suffering from inflammatory bowel disease, reduce the secretion of TNF-α, IL-6, IL-17 and IL-12/IL-23 pro-inflammatory factors, inhibit DC cell differentiation and migration, increase the ratio Foxp3+Treg cells, promote the movement of CD4+CD25+ Treg cells from the spleen and mesenteric lymph nodes to the colon, thereby inhibiting an intestinal inflammatory response and controlling the occurrence and development of the disease. When PDE9A inhibitor is applied to a drug for preventing and treating inflammatory bowel disease, inflammatory bowel disease may be effectively prevented, alleviated and treated, while healthcare products containing said inhibitor as an active ingredient may regulate the intestinal tract of patients suffering from inflammatory bowel disease and control the occurrence and development of inflammatory bowel disease.

12 Claims, 5 Drawing Sheets

| Name/ CAS NO | Chemical structure | PDE9 IC50 | Reference |
|---|---|---|---|
| PF-04447943 1082744-20-4 | 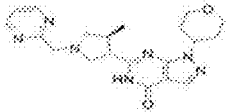 | 12 nM, 78 times more selective than other PDEs (IC50>1000 nM); | [1] Hutson P H, et al. 2011 [2] Kleiman RJ, et al. 2012. [3] Verhoest PR, et al. 2012 |
| PF-4181366 1082743-32-5 | 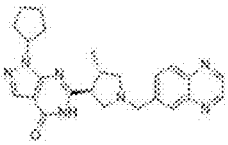 | 1.8 nM | Verhoest PR, et al. 2009 |
| BAY 73-6691 794568-92-6 | 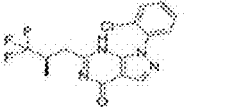 | 55 nM | Wunder F, et al. 2005. |
| PF-04449613 1236858-52-8 | 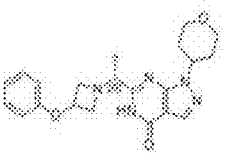 | 22 nM | Lai B, et al. 2018 |
| BI-409306 1169767-28-9 | 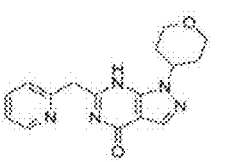 | 52 nM. It has a weak effect on other PDEs, including PDE1A ($IC_{50}$, 1.4 μM), PDE1C ($IC_{50}$, 1.0 μM), PDE2A, PDE3A, PDE4B, PDE5A, PDE6AB, PDE7A and PDE10A ($IC_{50}$ > 10 μM); | Dorner-Ciossek C, et al. 2015 |
| PDE9-IN-1 2305087-92-5 | 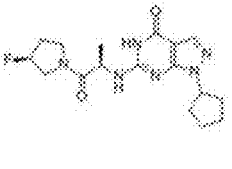 | 8.7 nM | Wu Y, et al. 2019 |
| (S)-C33 2066488-39-7 | 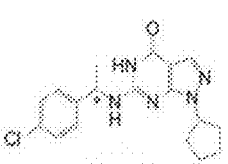 | 11 nM, 45 times more selective than other PDEs | Huang M, et al. 2015 |

Fig. 1

APPLICATION OF PDE9A INHIBITOR IN PREPARATION OF PRODUCTS HAVING ELEVATED TREG CONTENT, DRUGS FOR PREVENTING AND TREATING INFLAMMATORY BOWEL DISEASE AND HEALTH CARE PRODUCTS

CROSS REFERENCES TO RELATED APPLICATIONS

This application is the National Stage of International Application No. PCT/CN2019/095291, filed Jul. 9, 2019, and claims benefit of Chinese patent application submitted to the State Intellectual Property Office of China on Jul. 10, 2018 with an application number of 201810751621.1 and entitled "Application of PDE9A inhibitors in the preparation of products that increase the content of Treg, drugs and health care products for preventing and treating inflammatory bowel disease", the entire contents of both of which are hereby incorporated into this application by reference.

TECHNICAL FIELD

The invention relates to the field of medicine, and in particular to the application of PDE9A inhibitors in the preparation of products for increasing the amount of Treg, drugs for preventing and treating inflammatory bowel disease, and health care products.

TECHNICAL BACKGROUND

Regulatory cells (Tregs) are a subset of T cells that control autoimmune reactivity in vivo.

Inflammatory bowel disease (IBD) mainly includes ulcerative colitis and Crohn's disease (CD), a chronic idiopathic intestinal inflammatory disease that affects all parts of the intestine. The main clinical features of the disease include abdominal pain, diarrhea, weight loss, and rectal bleeding. Some patients may also have varying degrees of systemic symptoms. The etiology and pathogenesis of IBD are not fully understood. It is generally believed to be caused by a variety of factors, including genetic factors, immune factors, and infectious factors. Today's drugs for the treatment of IBD are mainly 5-aminosalicylic acid, adrenocortical hormone, immunosuppressive agents and biological agents. These drugs provide treatment for many patients, but more than 35% of patients are still unable to treat with existing drugs. The most widely used biological agents are TNF-αmonoclonal antibody preparations, including infliximab, adalimumab, certolizumab, etc., but some patients are insensitive to these biological agents. Other biologics include integrin antibodies, among which α4β7 integrin antibody vedolizumab was approved by the FDA in 2014 for the treatment of moderate to severe UC and CD, and patients treated with vedolizumab showed significant Clinical improvement, but 29% of UC patients and 37% of CD patients have adverse reactions.

Phosphodiesterases (PDEs) are enzymes that degrade intracellular cyclic nucleotides, such as cAMP and cGMP, and PDE cleaves 3'-phosphate by hydrolysis. The bond inactivates the cyclic nucleotide to form the corresponding inactive monophosphate product. Selective inhibition of PDEs by phosphodiesterase inhibitors (PDEI) causes intracellular cAMP and elevated levels of GMP to lead to enhanced protein kinase A/G (PKA/PKG) activation and protein phosphorylation, thereby inhibiting intracellular inflammatory responses. The PDE superfamily contains 11 gene families (PDE1 to PDE11), each of which contains 1 to 4 different genes. There are more than 20 genes in mammalian cells that encode more than 50 proteins, but each family occupies a different proportion in different tissues and cells.

The PDE9A cDNA was discovered in 1998 and named the ninth member of the PDE family. PDE9 is cGMP specific and, unlike other PDEs, it does not contain a protein domain of known function in the N-terminal region; the PDE domain is located at the C-terminal protein. PDE9 is encoded by a single gene, localized to human chromosome 21q22.3, and split into 25 exons that extend beyond 122 kb. Twenty-eight splice variants have been identified, and the longest transcript variant 1 (PDE9A1) is translated into a protein containing 593 amino acids. PDE9 expression is conserved across species, and PDE9 homologs have been found in primates, rodents, and fish. For example, homology in vertebrates is high, and human PDE9A2 is homologous to the corresponding mouse, with 93% and 83% at the amino acid and nucleotide levels, respectively. PDE9 mRNA was more or less detected in all organs; however, PDE9A had the highest signal in hematopoietic cells, brain, prostate, colon, small intestine, spleen, kidney and thymus.

In 2003, Pfizer confirmed that PDE9A inhibitors can play a role in the treatment of diabetes by gene knockout studies in mice, and reported the lead compound of the first PDE9A inhibitor. However, these compounds are less selective. Subsequently, in 2005 Bayer reported the first PDE9A selective inhibitor BAY73-6691 with an IC50 of 0.088 mM for PDE9A and 1.4 mM and 2.6 mM for PDE1C and PDE11A, respectively, and IC50 for other PDEs. Both are greater than 4.0 mM. To date, nearly 20 studies have reported the use of PDE9A inhibitors for the treatment of diseases such as diabetes, Alzheimer's disease, and Huntington's disease, and PDE9A is also considered a marker of heart failure, suggesting that PDE9A inhibitors may be used in the treatment of heart failure. But so far, there have been few studies on PDE9A in the intestine at home and abroad.

SUMMARY OF INVENTION

The object of the present invention is to provide a use of PDE9A inhibitors in preparation of product for enhancing the level of Treg (Regulatory Cell), which can be applied to the treatment of autoimmune diseases and for scientific research. The product comprises medicine, reagents or health products.

In one or more embodiments, the medicine further comprises conventional carrier in the pharmaceutical field, and the pharmaceutical carrier, which is selected from the group consisting of absorption enhancer, surfactant, lubricant, stabilizer, diluent, adhesive, wetting agent, disintegrant, adsorption vehicle, excipient, coloring agent, sweetener, and flavoring agent.

In one or more embodiments, the PDE9A inhibitor is selected from the group consisting of PDE9A inhibitor BAY 73-6691, PDE9A inhibitor PF-04447943, PDE9A inhibitor PF-04449613, PDE9A inhibitor PF-418366 and other PDE9A inhibitor. In one or more embodiments, the PDE9A inhibitor is at least one of PDE9A inhibitor BAY 73-6691, PDE9A inhibitor PF-04447943, PDE9A inhibitor PF-04449613, and PDE9A inhibitor PF-418366. For example, the PDE9A inhibitor is the PDE9A inhibitor PF_04447943.

In one or more embodiments, the medicine has a dosage form selected from the group consisting of injection, oral liquid, enema, capsule, tablet, enteric agent, powder and granule.

In one or more embodiments, the amount (or content) of Treg is related to the onset of autoimmune diseases such as rheumatoid arthritis, autoimmune thyroiditis, autoimmune liver disease, and various kidney diseases.

The present disclosure provides a method for increasing the amount (or level) of Treg, which comprises administering an effective amount of the above-mentioned product to a subject in need.

The present disclosure provides a use of PDE9A inhibitor in preparation of a medicine for preventing and treating inflammatory bowel disease, which can effectively prevent, alleviate and treat inflammatory bowel disease.

In one or more embodiments, the PDE9A inhibitor is selected from the group consisting of PDE9A inhibitor BAY73-6691, PDE9A inhibitor PF-04447943, PDE9A inhibitor PF-04449613, PDE9A inhibitor PF-418366, and other PDE9A inhibitors.

In one or more embodiments, the PDE9A inhibitor is at least one of the PDE9A inhibitor BAY73-6691, the PDE9A inhibitor PF-0447943, the PDE9A inhibitor PF-04449613, and the PDE9A inhibitor PF-418366. For example, the PDE9A inhibitor is the PDE9A inhibitor PF-04447943.

In one or more embodiments, the inflammatory bowel disease includes ulcerative colitis and/or Crohn's disease.

In one or more embodiments, the medicine for preventing and treating inflammatory bowel disease has a dosage form selected from injection liquid, oral liquid, enema, capsule, tablet, enteric agent, powder and granule.

In one or more embodiments, the drugs for preventing and treating inflammatory bowel disease also include conventional carrier in the pharmaceutical field, and the carrier is selected from the group consisting of absorption enhancer, surfactant, lubricant, stabilizer, diluent, adhesive, wetting agent, disintegrant, adsorption vehicle, excipient, coloring agent, sweetener, and flavoring agent.

The present disclosure provides a method for preventing and treating inflammatory bowel disease, which comprises administering an effective amount of the above-mentioned drug to a subject in need.

The present disclosure provides the application of PDE9A inhibitors in the preparation of health care products for regulating inflammatory bowel disease.

The health product can be used to regulate the intestinal tract of patients with inflammatory bowel disease and control the occurrence and development of inflammatory bowel disease.

In one or more embodiments, the PDE9A inhibitor is selected from the group consisting of PDE9A inhibitor BAY73-6691, PDE9A inhibitor PF-04447943, PDE9A inhibitor PF-044496 13, PDE9A inhibitor PF-418366 and other PDE9A inhibitors.

In one or more embodiments, the PDE9A inhibitor is at least one of PDE9A inhibitor BAY 73-6691, PDE9A inhibitor PF-04447943, PDE9A inhibitor PF-04449613, and PDE9A inhibitor PF-418366. For example, the PDE9A inhibitor is PDE9A inhibitor PF-04447943.

In one or more embodiments, the inflammatory bowel disease includes ulcerative colitis and/or Crohn's disease.

In one or more embodiments, the health care product further includes auxiliary materials selected from the group consisting of absorption enhancer, surfactant, lubricant, stabilizer, diluent, adhesive, wetting agent, disintegrant, adsorption vehicle, excipient, coloring agent, sweetener, and flavoring agent.

The present disclosure provides a method for regulating inflammatory bowel disease, which comprises administering an effective amount of the above-mentioned health product to a subject in need.

The beneficial effects of the embodiments of the present invention are as follows:

PDE9A inhibitors can improve the secretion of mucosal mucus in the intestinal tract of inflammatory bowel disease, reduce the secretion of TNF-α, IL-6, IL-17 and IL-12/IL-23 pro-inflammatory factors, increase SOD activity, reduce MDA amount (or level), and reduce DC cell differentiation, increase the proportion of Foxp3+Treg cells, increase the differentiation of Foxp3+Treg cells, and promote the migration of CD4+CD25+Treg cells from the spleen and mesenteric lymph nodes to the colon, thereby inhibiting the immune response and controlling the occurrence and development of the disease. When PDE9A inhibitors are used in drugs for the prevention and treatment of inflammatory bowel disease, they can effectively prevent, relieve and treat inflammatory bowel disease. At the same time, health care products containing it as an active ingredient can regulate the intestinal tract of patients with inflammatory bowel disease and control inflammation, the occurrence and development of enteropathy.

At the same time, because Treg is related to the onset of many autoimmune diseases such as rheumatoid arthritis, autoimmune thyroiditis, autoimmune liver disease, various kidney diseases, etc., PDE9A inhibitors are useful in the preparation of products that increase Treg amount and in-depth study thereof is helpful for understanding the pathogenesis of autoimmune diseases, thereby having far-reaching significance for the prognosis of the disease and further treatment.

DESCRIPTION OF FIGURES

In order to more clearly illustrate the technical solutions of the embodiments of the present invention, the drawings used in the embodiments will be briefly described below. It should be understood that the following drawings show only certain embodiments of the present invention, and therefore it should not be seen as a limitation on this scope, and ordinary technicians in this field can obtain other related drawings according to these drawings without any creative work.

FIG. 1 is a schematic diagram showing the specific structure, potency and selectivity of some PDE9A inhibitor;

DETAILED DESCRIPTION OF INVENTION

Figure 2:
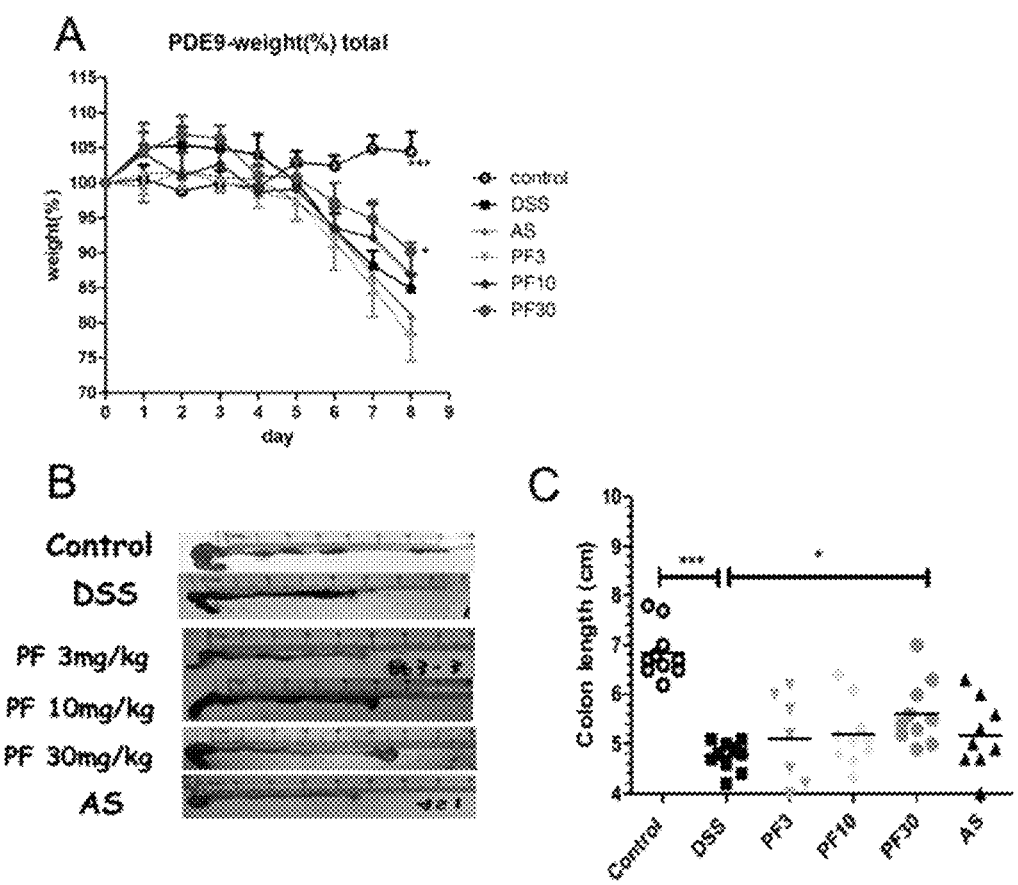
FIG. 2 is a comparison diagram of body weight and colon length of DSS modeled mice according to an embodiment of the present invention.

The technical solutions in the embodiments of the present invention will be clearly and completely described below in order to clarify the objects, the technical solutions and the advantages of the embodiments of the present invention. Those who do not specify the specific conditions in the examples are carried out according to the conventional conditions or the conditions recommended by the manufacturer. The reagents or instruments used are not indicated by the manufacturer, and are conventional products that can be obtained by commercially available purchase.

The application of the PDE9A inhibitor of the embodiment of the present invention in the preparation of a drug or a reagent for increasing the Treg amount, a drug for preventing and treating inflammatory bowel disease, and a health care product will be specifically described below.

It is an object of the present invention to provide a PDE9A inhibitor for use in the manufacture of a medicament or agent for increasing the amount (or content) of a Treg (Regulatory Cell) for the treatment of diseases such as inflammatory bowel disease, and for scientific research. At the same time, Treg is associated with many autoimmune diseases such as rheumatoid arthritis, autoimmune thyroiditis, autoimmune liver disease, and various kidney diseases. Therefore, the application of PDE9A inhibitor in the preparation of reagents for increasing Treg amount, In-depth study of it will help to understand the pathogenesis of autoimmune diseases, and has far-reaching significance for disease prognosis and further treatment. At the same time, the application of PDE9A inhibitors in the preparation of drugs for increasing Treg amount can be further studied in the future for the treatment of autoimmune diseases associated with them.

There are many PDE9 inhibitors that can be purchased directly or designed accordingly. Among them, preferably, the PDE9A (phosphodiesterase 9A) inhibitor is one selected from the group consisting of a PDE9A inhibitor BAY 73-6691, a PDE9A inhibitor PF-04447943, a PDE9A inhibitor PF-04449613, and a PDE9A inhibitor PF-418366. But do not rule out other PDE9A inhibitor. For example, the PDE9A inhibitor is a mixture of PDE9A inhibitor BAY 73-6691 and PDE9A inhibitor PF-04447943, PDE9A inhibitor PF-04447943, PDE9A inhibitor PF-04449613 and PDE9A inhibitor PF-418366, PDE9A inhibitor PF-04447943 or PDE9A inhibitor PF-418366, etc., wherein the specific structure, potency and selectivity of each PDE9A inhibitor are shown in FIG. 1.

The present disclosure provides a method for increasing the amount (or level) of Treg, which comprises administering an effective amount of the above-mentioned product to a subject in need.

The present disclosure provides the application of products including PDE9A inhibitors in increasing the amount of Treg.

The invention provides the use of a PDE9A inhibitor in the preparation of a medicament for preventing and treating inflammatory bowel disease, wherein the prevention and treatment comprises preventing the occurrence of inflammatory bowel disease, treating inflammatory bowel disease and reducing symptoms of inflammatory bowel disease (i.e., relieving symptoms). That is, PDE9A inhibitors can effectively prevent, alleviate and treat inflammatory bowel disease.

There are many PDE9 inhibitors that can be purchased directly or designed accordingly. Among them, preferably, the PDE9A (phosphodiesterase 9A) inhibitor is one selected from the group consisting of a PDE9A inhibitor BAY 73-6691, a PDE9A inhibitor PF-04447943, a PDE9A inhibitor PF-04449613, and a PDE9A inhibitor PF-418366, But do not rule out other PDE9A inhibitor. For example, the PDE9A inhibitor is a mixture of PDE9A inhibitor BAY 73-6691 and PDE9A inhibitor PF-04447943, PDE9A inhibitor PF-04447943, PDE9A inhibitor PF-04449613 and PDE9A inhibitor PF-418366, PDE9A inhibitor PF-04447943 or PDE9A inhibitor PF-418366, etc., wherein the specific structure, potency and selectivity of each PDE9A inhibitor are shown in FIG. 1.

In a preferred embodiment of the invention, the PDE9 inhibitor PF-04447943 has entered clinical studies, and thus the PDE9A inhibitor is preferably the PDE9A inhibitor PF-04447943.

Inflammatory bowel disease includes ulcerative colitis and/or Crohn's disease, and it can be deduced that it can also alleviate other complications such as ulcerative colitis and/or Crohn's disease.

In a preferred embodiment of the present invention, the dosage form of the medicament for preventing and treating inflammatory bowel disease includes an injection solution, an oral solution, an enema solution, a capsule, a tablet, an enteric solvent, a powder or a granule. It is preferably an oral liquid preparation, a capsule, a tablet, an enteric solvent, a powder or a granule, which is directly orally administered and is convenient to take.

In a preferred embodiment of the present invention, the medicament for preventing and treating inflammatory bowel disease further comprises conventional excipients in the pharmaceutical field, and the auxiliary materials include absorption enhancers, surfactants, lubricants, stabilizers, diluents, binders, wetting agents, and collapses. At least one of a decomposing agent, an adsorbent carrier, an excipient, a coloring matter, a sweetener, and a flavoring agent can be produced in different dosage forms using existing processes and equipment.

The present invention provides a method for preventing and treating inflammatory bowel disease, which comprises administering an effective amount of the above-mentioned drug to a subject in need.

The present invention provides the application of drugs including PDE9A inhibitors in the prevention and treatment of inflammatory bowel disease.

Further, the present invention provides a use of a PDE9A inhibitor for the preparation of a health care product for modulating inflammatory bowel disease.

Among them, preferably, the PDE9A (phosphodiesterase 9A) inhibitor is one selected from the group consisting of a PDE9A inhibitor BAY 73-6691, a PDE9A inhibitor PF-04447943, a PDE9A inhibitor PF-04449613, and a PDE9A inhibitor PF-418366, but do not rule out other PDE9A inhibitor. For example, the PDE9A inhibitor is a mixture of PDE9A inhibitor BAY 73-6691 and PDE9A inhibitor PF-04447943, PDE9A inhibitor PF-04447943, PDE9A inhibitor PF-04449613 and PDE9A inhibitor PF-418366, PDE9A inhibitor PF-04447943 or PDE9A inhibitor PF-418366, etc., wherein the specific structure, potency and selectivity of each PDE9A inhibitor are shown in FIG. 1.

In a preferred embodiment of the invention, the PDE9 inhibitor PF-04447943 has entered clinical studies, and thus the PDE9A inhibitor is preferably the PDE9A inhibitor PF-04447943.

In view of the above, it should be noted that the inflammatory bowel disease referred to in the present invention includes ulcerative colitis and/or Crohn's disease. At the same time, it can be deduced that it can alleviate other complications such as ulcerative colitis and/or Crohn's disease.

The present disclosure provides a method for regulating inflammatory bowel disease, which comprises administering an effective amount of the above-mentioned health product to a subject in need.

The present disclosure provides the application of health care products including PDE9A inhibitors in the regulation of inflammatory bowel disease.

The features and performance of the present invention are further described in detail below in conjunction with the Examples.

Example 1

C57 female mice were selected and weighed about 20 g. All mice were randomly divided into control group (control group), model group (DSS group), sulfasalazine group (AS group) and low dose group (PF3 group). The middle dose group (PF10 group) and the high dose group (PF30 group), a total of 6 groups, 10 mice in each group.

The control group was treated with deionized water and the remaining 5 groups were fed with 3% DSS solution.

During the period, the sulfasalazine group was intragastrically administered at a dose of 0.5 g/kg, and the PF-04447943 low-dose group, the middle-dose group, and the high-dose daily gavage were administered at a dose of 3 mg/kg, 10 mg/kg, and 30 mg/kg, respectively. The body weight, water bottle weight and the record were weighed daily. On the 8th day, the mice were sacrificed by deep anesthesia, and the colon, mesenteric lymph nodes, spleen and anus were taken. The length of the colon was measured and the colon was divided into three sections. The anal part specimens were fixed in formalin and the remaining specimens were stored frozen at −80° C. Isolating the mononuclear cells of colon, mesenteric lymph node and spleen, then staining separately, the distribution of DC cells and Treg cells in colon, mesenteric lymph nodes and spleen were determined by flow cytometry. IL-6, IL-12, TNF-α, IL-17 etc were measured by ELISA. SOD activity and MDA amount in colon tissue were measured, and the effect of PDE9A inhibitor PF-04447943 on mouse model was analyzed.

(1) DSS Induced Model Weight and Colon Length Test

FIG. 2 is a control plot of body weight and colon length of DSS modeled mice, wherein FIG. 2(C) is $*P<0.0.5$; $P<0.01$; $*P<0.001$ vs DSS model group.

Referring to FIG. 2(A), it can be seen that the body weight of the control mice fluctuated above the initial body weight, while the other 5 groups of mice used DSS, AS 0.5 g/kg, PF-04447943 3 mg/after 7 days. After kg, PF-04447943 10 mg/kg and PF-04447943 30 mg/kg, body weight began to decrease significantly on the 5th day. The weight results before sacrifice on day 7 showed that there was a significant difference in the body weight of the PF-04447943 30 mg/kg group compared with the model group, which had a certain improvement effect.

Referring to FIGS. 2(B and C), by analyzing the colon length of mice, the colon of DSS was significantly shortened after DSS modeling, and there was a significant difference compared with the normal group. There was a significant difference in colon length between DSS group and PF30 group. This indicates that PF-04447943 may have a protective effect on the colon of DSS model mice.

In conclusion, the PDE9A inhibitor PF-04447943 inhibited the weight loss and colon shortening in the DSS-induced model.

(2) Intestinal Mucin Secretion Test in DSS-Induced Model

Figure 3:
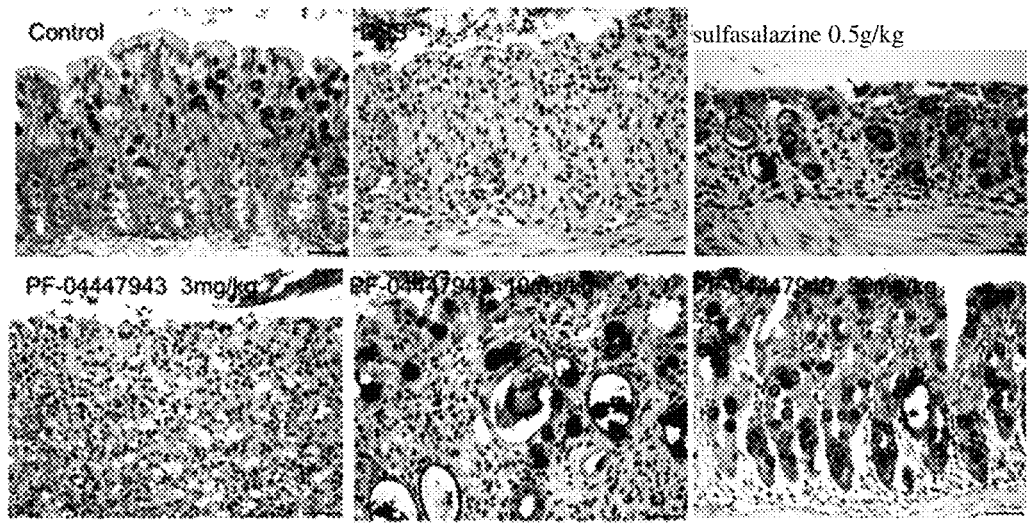
FIG. 3 is a control diagram of colonic mucin secretion in DSS modeled mice according to an embodiment of the present invention.

FIG. 3 is a control map of colonic mucin secretion in DSS model mice. It can be obtained from FIG. 3. The DSS group lost epithelial integrity, crypt structure, and goblet cell, company with immune cell infiltration, Smooth muscle cell hypertrophy and reduced secretory glycoprotein when compared with the control group. The loss of epithelial integrity and crypt structure in the low-dose, medium-dose, and high-dose groups, the loss of goblet cells, immune cell infiltration, and smooth muscle cell hypertrophy and secretory glycoprotein reduction were gradually reversed, and as the dose of PF-04447943 increases, the protective effect on colonic epithelial cells is gradually better. At the same time, the degree of protection of the colonic epithelium in the sulfasalazine group was similar to that in the PF-04447943 medium dose group, but not better than that in the PF-04447943 high dose group.

According to the above, PF-04447943 can significantly inhibit the destruction of intestinal mucosal mucin secretion induced by DSS.

Figure 4:
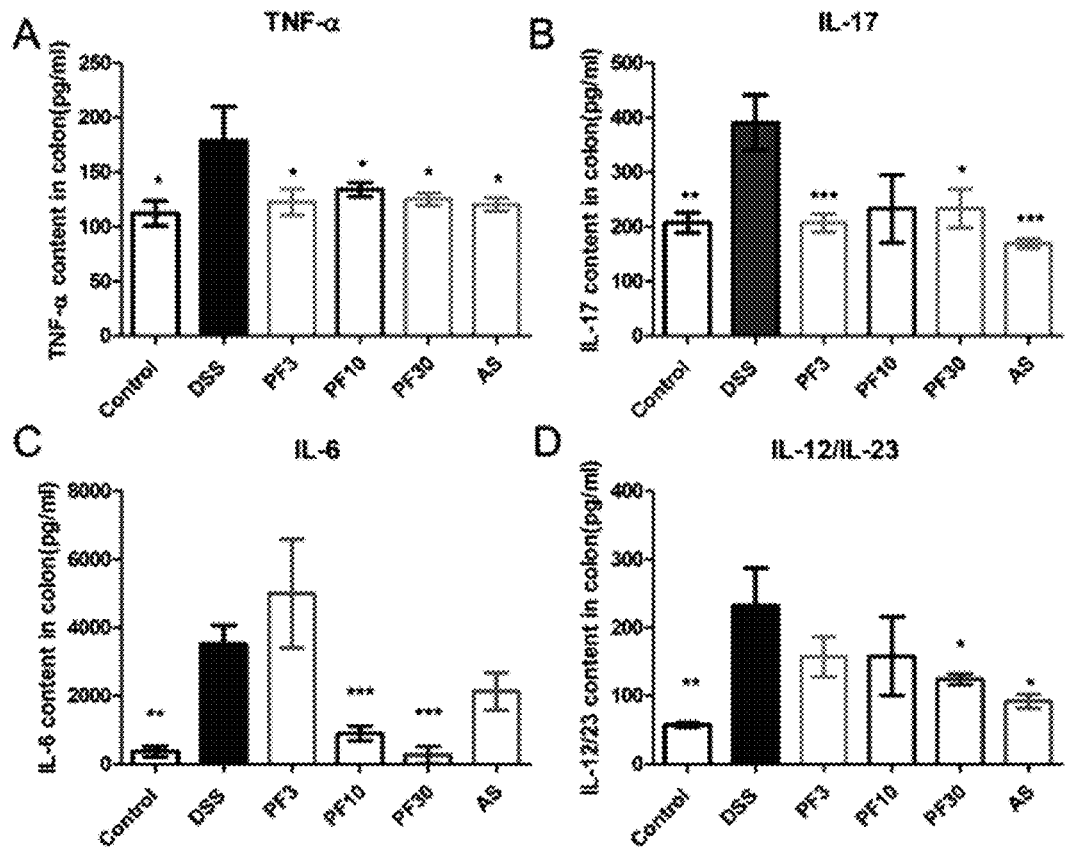
FIG. 4 is a control diagram of inflammatory factors secreted by the intestinal mucosa of DSS modeled mice according to an embodiment of the present invention.

(3) Trial of Inflammatory Factors Secreted By Intestinal Mucosa in DSS-Induced Model FIG. 4 is a control map of inflammatory factors secreted by the intestinal mucosa of DSS model mice, wherein, in FIG. 4(A to D), $*P<0.05$; $P<0.01$; $*P<0.001$ vs. DSS model group.

After intestinal tissue homogenization, TNF-α, IL-17, IL-6, IL-12/IL-23 in colon tissue were determined by ELISA kit.

Please refer to FIG. 4(A to D) together. The TNF-α, IL-17, IL-6, IL-12/IL-23 in the DSS group were significantly higher than those in the control group. The levels of sputum, IL-17, IL-6, IL-12/IL-23 were lower than those in the DSS group, and the high dose group was statistically significant compared with the DSS group. The inhibitory effect of PF-04447943 on IL-6 was significant. The IL-6 levels in the middle dose group and the high dose group were significantly lower than those in the DSS group. It is suggested that in the DSS model, PF-04447943 inhibits the onset of inflammation by inhibiting pro-inflammatory cytokines. At the same time, since these cytokines are derived from TH1, TH2 and TH17, respectively, this result also suggests that PF-04447943 has a certain inhibitory effect on TH1, TH2 and TH17.

In conclusion, this experiment demonstrates that PF-04447943 significantly inhibits DSS-induced inflammatory factors secreted by the intestinal mucosa.

(4) Activation Test of Intestinal Mucosa DC in DSS Induced Model

The colon was digested with collagenase, and the mesenteric lymph nodes were ground and sieved through 100 mesh to prepare single cell suspensions. The cell density was adjusted to 105/100 μl, and the DC cell amount was determined for each sample.

Figure 5:
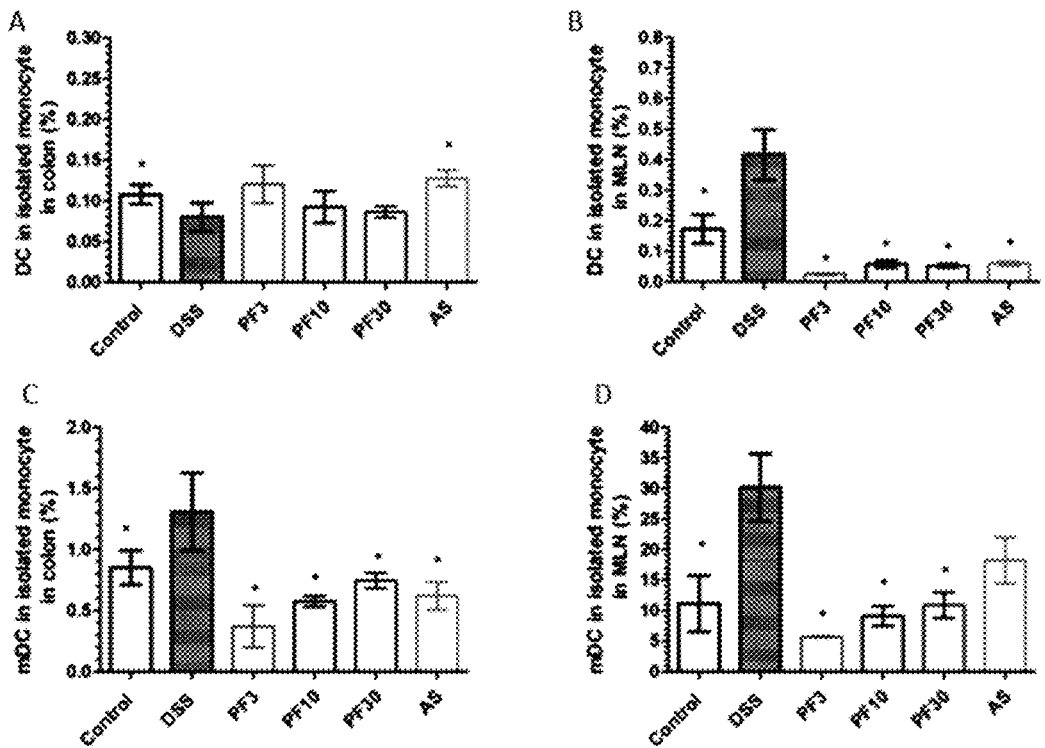
FIG. 5 is a control diagram of total DC and mature DC in colon and mesenteric lymphatic cleansing of DSS modeled mice according to an embodiment of the present invention.

FIG. 5 is a control plot of total DC and mature DC in colon, mesenteric lymphatic cleansing in DSS model mice. In FIG. 5, $*P<0.0.5$; $P<0.01$; $*P<0.001$ vs DSS model group.

As can be seen from FIGS. 5(A and C), in the colon, the control group had more total DC cells than the DSS group, but the activated DC (mDC) cells were significantly lower than the DSS group, while the low, medium and high dose groups were activated DC cells were also significantly lower than the DSS group, and DC cells activated with increasing doses increased the DC cells activated by the sulfasalazine group compared with the middle dose group but lower than the high dose group.

According to FIGS. 5(B and D), in the mesenteric lymph node (MLN), the total DC cell DSS group was significantly higher than the control group, while the low, medium and high groups were significantly lower than the DSS group. It is suggested that drug treatment can inhibit the migration of DC. The activated DC cell control group was significantly lower than the DSS group, and the high, medium and low dose groups were significantly lower than the DSS group. Activated DC cells were lower and statistically significant in DSS than in the low, medium, and high dose groups, both in the colon and in the mesenteric lymph nodes. The results of the sulfasalazine group were similar to those in the low, medium, and high groups. PF-04447943 can inhibit the migration of DC cells from the colon to the mesenteric lymph nodes, as well as the maturation of the colon and mesenteric lymph nodes.

(5) Activation Test of Treg in DSS Induction Model

The colon was digested with collagenase, and the mesenteric lymph nodes and spleen tissues were ground and sieved through 100 mesh to prepare single cell suspensions. The cell density was adjusted to $10^5$ cell/100 μl, and the Treg amount was determined for each sample.

Figure 6:
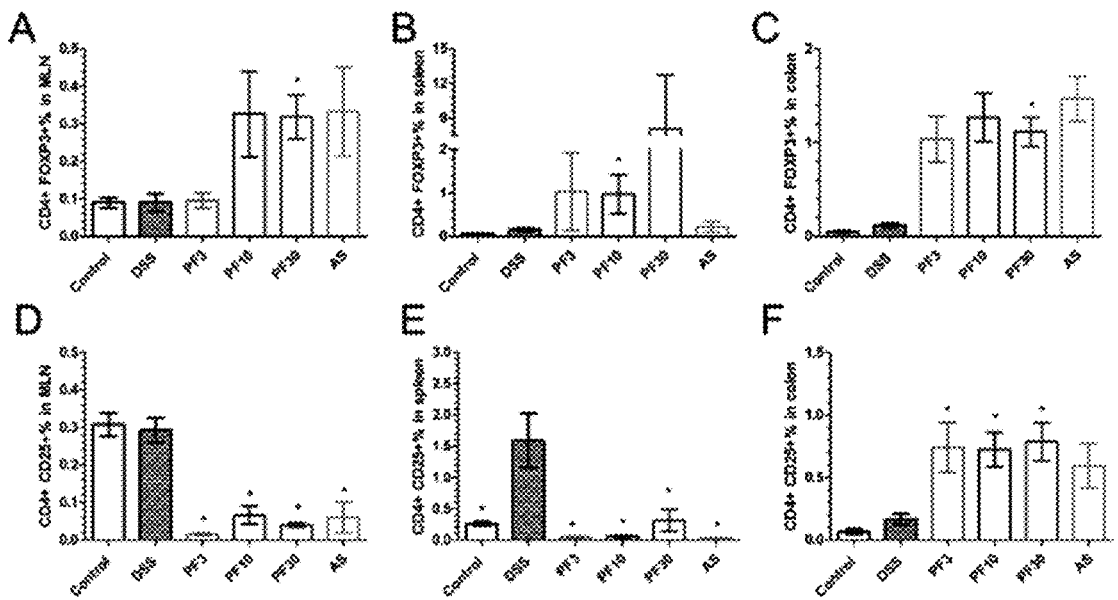
FIG. 6 is a control diagram of the amount of Tregs in the mesenteric lymphatic cleansing, spleen and colon of DSS modeled mice according to an embodiment of the present invention.

Related studies have shown that T cells, especially Treg cells, play a role in the protection of DSS inflammatory bowel disease model. In order to study the role of Treg in the DSS colitis model, three mesenteric lymph nodes, spleen and colon were evaluated based on trial 4, respectively. The distribution of Treg cell subsets in the mesenteric lymph node, spleen and colon are shown in FIG. 6. FIG. 6 is a control plot of the number of Tregs in the mesenteric lymph node, spleen and colon of DSS model mice, Note: *$P<0.0.5$; $P<0.01$; *$P<0.001$ vs DSS model group.

As shown in FIGS. 6(A, B, and C), there was no significant difference in CD4+Foxp3+ Treg cells between the DSS group and the control group. CD4+FOXP3+ Treg cells were in the high dose group of PF-04447943 in the mesenteric lymph nodes, spleen, and colon, significantly higher than that of the DSS group and the control group.

As shown in FIGS. 6(D, E and F), CD4+CD25+ Treg cells were significantly lower in the high, medium and low dose groups of mesenteric lymph nodes and spleen than in the control and DSS groups, but significantly higher in the colon than in the DSS group in the control group. PF-04447943 significantly induced an increase in the differentiation of CD4+Foxp3+ Treg cells. CD4+CD25+Treg cells mainly inhibit immunosuppression. Oral PF-04447943 allows more CD4+CD25+ Treg cells to move from the spleen and mesenteric lymph nodes to the colon, exerting its immunosuppressive effect. That is, Test 5 showed that PF-04447943 significantly enhanced DSS-inhibited Treg activation, thereby protecting the DSS inflammatory bowel disease model.

(6) Test of SOD Activity and MDA Amount in Colon Tissue of DSS-Induced Model

Figure 7:
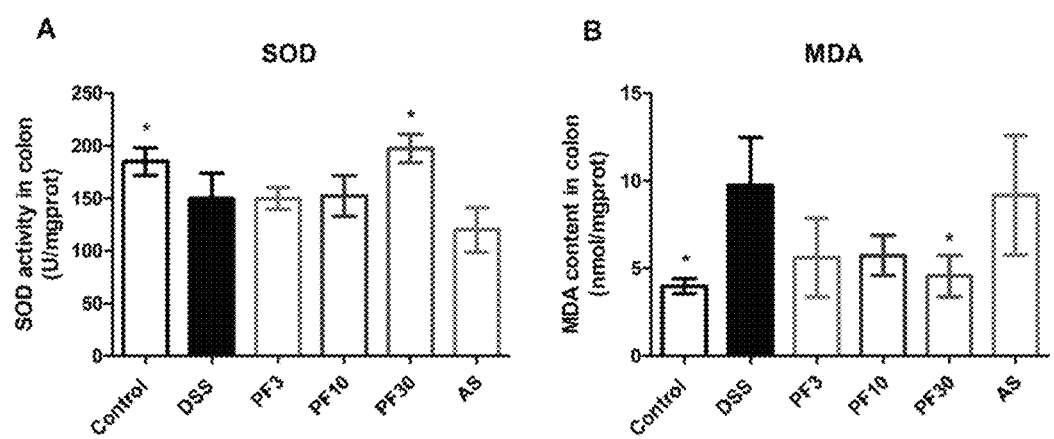
FIG. 7 is a comparison diagram of SOD activity and MDA amount in a colon tissue homogenate of DSS modeled mice according to an embodiment of the present invention.

FIG. 7 is a control plot of SOD activity and MDA amount in intestinal mucosa of DSS model mice, wherein, in FIG. 7(A to B), *$P<0.0.5$; $P<0.01$; *$P<0.001$ Vs DSS model group.

After the intestinal tissue homogenization, SOD activity and MDA amount in colon tissue were determined by SOD and MDA assay kits.

Referring to FIG. 7(A), the SOD activity in the DSS group was significantly decreased, and the SOD activity in the high dose group was improved compared with the DSS group, which was statistically significant compared with the DSS group. PF-04447943 significantly increased the activity of SOD in colon tissue. Referring to FIG. 7(B), the MDA amount in the DSS group was significantly higher than that in the control group. The MDA amount of the drug group was lower than that of the DSS group, and the high dose group was statistically different from the DSS group. The inhibitory effect of PF-04447943 on MDA was significant, and the MDA amount was significantly lower than that of the DSS group. It is suggested that in the DSS model, PF-04447943 has strong anti-oxidation function, inhibits MDA amount and inhibits inflammation by enhancing SOD activity. Therefore, this result also suggests that PF-04447943 has a strong antioxidant function.

According to the above, this experiment shows that PF-04447943 can significantly inhibit DSS-induced intestinal oxidative stress damage.

In summary, oral administration of PF-04447943 can improve mucus secretion in the intestinal mucosa of DSS mice, reduce the secretion of TNF-α, IL-6, IL-17 and IL-12/IL-23 pro-inflammatory factors, and increase SOD activity. Decreased MDA amount, decreased DC cell differentiation, increased the proportion of Foxp3+ Treg cells, and promoted the movement of CD4+CD25+ Treg cells from the spleen and mesenteric lymph nodes to the colon, thereby suppressing the immune response and controlling the occurrence and development of the disease. From the above results, it can be inferred that PDE9A inhibitor can improve the symptoms of inflammatory bowel disease (IBD) and can be used for the treatment of IBD. The efficacy of the high-dose PF-04447943 group in IL-6 secretion, SOD activity, MDA amount, the activation of DC and the regulation of Treg are superior to the conventional drug sulfasalazine at conventional dose.

Based on the results of the animal test, it is known that the PDE9A inhibitor has a good activity for preventing and treating inflammatory bowel disease. Therefore, it is inferred that the PDE9A inhibitor as an active ingredient can prevent, alleviate and treat inflammatory bowel disease when it is used in the prevention and treatment of inflammatory bowel disease.

It can be inferred from the above that PDE9A inhibitors are bound to be used in the preparation of health care products for conditioning inflammatory bowel disease, to regulate the intestinal tract of patients with inflammatory bowel disease, and to control the occurrence and development of inflammatory bowel disease.

In summary, the embodiments of the present invention provide a PDE9A inhibitor for the preparation of a medicament for preventing and treating inflammatory bowel disease and a health care product for regulating inflammatory bowel disease, which can effectively prevent, alleviate and treat inflammatory bowel disease, and simultaneously the health care product can regulate the intestinal tract of patients with inflammatory bowel disease and control the occurrence and development of inflammatory bowel disease. At the same time, the application of PDE9A inhibitors in the preparation of drugs or agents for increasing the amount of Treg can be applied to the treatment of autoimmune diseases and for scientific research.

The embodiments described above are a part of the embodiments of the invention, and not all of the embodiments. The detailed description of the embodiments of the invention is not intended to limit the scope of present invention, but is to illustrate certain examples of the invention. All other embodiments obtained by ordinary technicians in this field based on the embodiments of the present invention without creative efforts are within the scope of the present invention.

INDUSTRIAL APPLICABILITY

When PDE9A inhibitors are used in drugs for the prevention and treatment of inflammatory bowel disease, they can effectively prevent, relieve and treat inflammatory bowel disease. At the same time, health products containing it as an active ingredient can regulate the intestinal tract of patients with inflammatory bowel disease and control inflammation, the occurrence and development of enteropathy. At the same time, because Treg is related to the onset of many autoimmune diseases such as rheumatoid arthritis, autoimmune thyroiditis, autoimmune liver disease, various kidney diseases, etc., PDE9A inhibitors are useful in the preparation of products that increase the amount of Treg. Application and in-depth research on it will help to understand the pathogenesis of autoimmune diseases, and have profound significance for the prognosis of the disease and further treatment.

The invention claimed is:

1. A method for increasing Treg amount, which comprises administering an effective amount of PDE9A inhibitor PF-04447943 or a product comprising PDE9A inhibitor PF-04447943 to a subject in need.

2. The method of claim 1, wherein the product comprises a medicine, a reagent, or a health care product.

3. The method of claim 2, wherein the medicine comprises PDE9A inhibitor PF-04447943 and a pharmaceutical carrier.

4. The method of claim 3, wherein the pharmaceutical carrier is selected from the group consisting of: an absorption enhancer, a surfactant, a lubricant, a stabilizer, a diluent, an adhesive, a wetting agent, a disintegrant, an adsorption vehicle, an excipient, a coloring agent, a sweetener, and a flavoring agent.

5. The method of claim 2, wherein the medicine has a dosage form selected from the group consisting of: an injection, an oral liquid, an enema, a capsule, a tablet, an enteric agent, a powder, and a granule.

6. The method of claim 1, wherein the amount of Treg is related to the onset of an autoimmune disease selected from the group consisting of: rheumatoid arthritis, autoimmune thyroiditis, autoimmune liver disease, and kidney disease.

7. A method for treating a Treg related disease, which comprises administering an effective amount of PDE9A inhibitor PF-04447943 or a pharmaceutical composition comprising PDE9A inhibitor PF-04447943 to a subject in need,
wherein the Treg related disease is selected from the group consisting of: inflammatory bowel disease, rheumatoid arthritis, autoimmune thyroiditis, autoimmune liver disease, and kidney disease.

8. The method of claim 7, wherein the Treg related disease is inflammatory bowel disease.

9. The method of claim 8, wherein the inflammatory bowel disease is ulcerative colitis or Crohn's disease.

10. The method of claim 7, wherein the pharmaceutical composition comprises PDE9A inhibitor PF-04447943 and a pharmaceutical carrier.

11. A method for regulating inflammatory bowel disease, which comprises administering an effective amount of a health care product comprising PDE9A inhibitor PF-04447943 to a subject in need.

12. The method of claim 11, wherein the health care product further comprises an auxiliary material selected from the group consisting of: an absorption enhancer, a surfactant, a lubricant, a stabilizer, a diluent, an adhesive, a wetting agent, a disintegrant, an adsorption vehicle, an excipient, a coloring agent, a sweetener, and a flavoring agent.

* * * * *